United States Patent
Saleh

(10) Patent No.: US 11,124,499 B2
(45) Date of Patent: Sep. 21, 2021

(54) **PHARMACEUTICAL COMPOSITION DERIVED FROM *TECOMA* PLANT AND A METHOD FOR TREATING CANCER**

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Ayman Mahmoud Saleh, Jeddah (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 28 days.

(21) Appl. No.: 16/570,376

(22) Filed: Sep. 13, 2019

(65) Prior Publication Data
US 2020/0247786 A1    Aug. 6, 2020

Related U.S. Application Data

(60) Provisional application No. 62/730,809, filed on Sep. 13, 2018.

(51) Int. Cl.
*C07D 403/14* (2006.01)
*A61P 35/02* (2006.01)

(52) U.S. Cl.
CPC ............ *C07D 403/14* (2013.01); *A61P 35/02* (2018.01)

(58) Field of Classification Search
USPC .......................................................... 514/414
See application file for complete search history.

(56) References Cited

FOREIGN PATENT DOCUMENTS

WO    WO 2013/144595 A1    10/2013
WO    WO 2017/031173 A1    2/2017

OTHER PUBLICATIONS

Jones (Magnesium 2,4-Divinylphaeoporphyrin a5 Monomethyl Ester, a Protochlorophyll-like Pigment Produced by Rhodopseudomonas spheroids, Mar. 1963).*

Harsh Garg, et al., "The C2$^1$-formyl group in chlorophyll f originates from molecular oxygen", Journal of Biological Chemistry, vol. 292, No. 47, 2017, pp. 19279-19289.

Benjamin M. Wolf, et al., "Characterization of a newly isolated freshwater Eustigmatophyte alga capable of utilizing far-red light as its sole light source", Photosynthesis Research, vol. 135, Nos. 1-3, 2018, pp. 177-189 (Abstract only).

Jesús Pascual, et al., "Integrated Physiological, Proteomic, and Metabolomic Analysis of Ultra Violet (UV) Stress Responses and Adaptation Mechanisms in *Pinus radiate*", Molecular & Cellular Proteomics, vol. 16, No. 3, 2017, pp. 485-501.

Jian Yang, et al., "Effect of Chlorophyll Concentration of Paddy Rice on Fluorescence Spectrum", Guangpuxue Yu Guangpu Fenxi, vol. 36, No. 10, Oct. 2016, pp. 3410-3413 (Abstract only).

Roman A. Voloshin, et al., "Photoelectrochemical cells based on photosynthetic systems: a review", Biofuel Research Journal, vol. 6, 2015, pp. 227-235.

Yaqiong Li, et al., "Characterization of red-shifted phycobilisomes isolated from the chlorophyll f-containing cyanobacterium *Halomicronema hongdechloris*", Biochimica Et Biophysica Acta, vol. 1857, No. 1, 2016, pp. 107-114.

Fei Gan, et al., "Adaptive and acclimative responses of cyanobacteria to far-red light", Environmental Microbiology, vol. 17, No. 10, Oct. 2015, pp. 3450-3465 (Abstract only).

Lars Behrendt, et al., "Chlorophyll f-driven photosynthesis in a cavernous cyanobacterium", The ISME Journal, vol. 9, Issue 9, Feb. 2015, pp. 1-9.

Hideaki Miyashita, et al., "Discovery of Chlorophyll d in *Acaryochloris marina* and Chlorophyll f in a Unicellular Cyanobacterium, Strain KC1, Isolated from Lake Biwa", Journal of Physical Chemistry & Biophysics, vol. 4, Issue 4, 2014, pp. 1-9.

Kana Sadaoka, et al., "Effects of the central metal on stretching vibrational bands of the peripheral carbonyl moieties in formylated chlorophyll derivatives studied by Fourier-transform infrared spectroscopy", Journal of Porphyrins and Phthalocyanines, vol. 18, No. 06, 2014, pp. 506-512 (Abstract only).

Martin Schliep, et al, "Formyl group modification of chlorophyll a: a major evolutionary mechanism in oxygenic photosynthesis", Plant, Cell & Environment, vol. 36, Issue 3, 2013, pp. 521-527 (Abstract/Introduction only).

Ryouichi Tanaka, et al., "Chlorophyll Metabolism in Photosynthetic Organisms", Handbook of Porphyrin Science, vol. 20, 2012, pp. 213-242 (Abstract only).

Shinya Akutsu, et al., "Pigment analysis of a chlorophyll f-containing cyanobacterium strain KC1 isolated from Lake Biwa", Photomedicine and Photobiology, vol. 33, 2011, pp. 35-40 (Abstract only).

Lorentz Jäntschi, et al., "Chlorophylls—natural solar cells", Bulletin of University of Agricultural Sciences and Veterinary Medicine Cluj-Napoca, Agriculture, vol. 68, No. 1, 2011, pp. 181-187.

Ujjal Kumar Sur, "A near-infrared light photosynthetic pigment", Current Science, vol. 100, No. 3, Feb. 10, 2011, pp. 286-287.

(Continued)

*Primary Examiner* — Kathrien A Cruz
(74) *Attorney, Agent, or Firm* — Oblon, McClelland, Maier & Neustadt, L.L.P.

(57) ABSTRACT

A pharmaceutical composition containing an anti-proliferative compound, named Tecomaphorbide, which is identified and isolated from *Tecoma* plants (e.g. *Tecoma stans*). The pharmaceutical composition may contain a derivative and/or a salt of Tecomaphorbide. A process of obtaining Tecomaphorbide from *Tecoma* plants is specified. A method of treating cancer (e.g. leukemia, lymphoma, breast, colon, and prostate cancer) with the pharmaceutical composition is also provided.

13 Claims, 2 Drawing Sheets

(56) References Cited

OTHER PUBLICATIONS

Min Chen, et al., "A Red-Shifted Chlorophyll", Science, vol. 329, Sep. 10, 2010, pp. 1318-1319.
0. T. G. Jones, "Magnesium 2,4-Divinylpheoporphyrin $a_5$ Monomethyl Ester, a Protochlorophyll-like Pigment Produced by *Rhodopseudomonas spheroides*", Biochemical Journal, vol. 89, No. 2, 1963, pp. 182-189.

\* cited by examiner

PHARMACEUTICAL COMPOSITION DERIVED FROM *TECOMA* PLANT AND A METHOD FOR TREATING CANCER

CROSS REFERENCE TO RELATED APPLICATIONS

This application claims the benefit of priority of U.S. Provisional Application No. 62/730,809 filed on Sep. 13, 2018, the entire contents of which are herein incorporated by reference.

STATEMENT OF FUNDING ACKNOWLEDGEMENT

This project was funded by King Abdullah International Medical Research Center (KAIMRC), Riyadh, Saudi Arabia, under grant number RC12/159.

BACKGROUND OF THE INVENTION

Technical Field

The present disclosure relates to a pharmaceutical composition which contains a natural product with anti-proliferative activity and an exogenous pharmaceutically acceptable carrier and/or excipient. The present disclosure relates to a method of identifying and isolating the natural product from a *Tecoma* plant and a method of treating proliferative disorders.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Medicinal plants are major sources of bioactive molecules with diverse and complex structures that are often challenging to synthesize by existing methodologies. Because of their therapeutic benefits, medicinal plants are used as active components in many traditional medicines. Moreover, investigation of these naturally-occurring molecules supports modern drug discovery and development.

*Tecoma stans* is a perennial shrub in the trumpet vine family that is cultivated as an ornamental plant. Several previous studies have tested the anti-hyperglycemic, anti-proliferative, antioxidant, and antimicrobial properties of *Tecoma stans*. However, research efforts have been focused on therapeutic efficacies of various plant extracts (e.g. leaf, flower, bark, root extracts) of *Tecoma stans*. Therefore, there is a need to identify, isolate, and purify individual compound(s) to treat diseases such as cancer with enhanced therapeutic potency, drug specificity, and clinical safety.

In view of the forgoing, one objective of the present disclosure is to provide a pharmaceutical composition containing a bioactive compound found in *Tecoma* plants. Another objective of the present disclosure is to provide a method of isolating the bioactive compound and a method of treating proliferative disorders such as cancer using the pharmaceutical composition.

BRIEF SUMMARY OF THE INVENTION

According to a first aspect, the present disclosure relates to a pharmaceutical composition comprising a compound of formula (I)

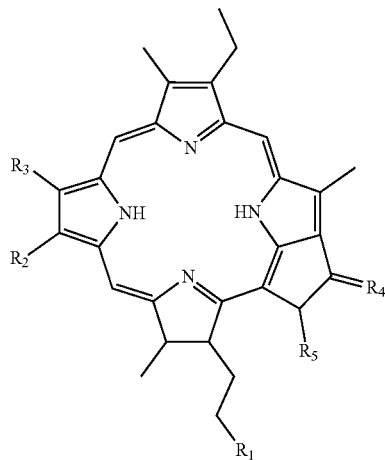

or a salt thereof, a solvate thereof, a tautomer thereof, a stereoisomer thereof, or a mixture thereof, and an exogenous pharmaceutically acceptable carrier and/or excipient which is not present in *Tacoma stans*, wherein (i) $R_1$ and $R_5$ are independently selected from the group consisting of an optionally substituted alkoxycarbonyl, an optionally substituted aryloxycarbonyl, a carboxy, and an optionally substituted carbamyl, with the proviso that $R_1$ is neither —COO$(CH_2)_{19}CH_3$, nor —COOCH$_2$—CH=C(CH$_3$)—(CH$_2$)$_3$CH(CH$_3$)—(CH$_2$)$_3$CH(CH$_3$)—(CH$_2$)$_3$CH(CH$_3$)$_2$, (ii) $R_2$ is selected from the group consisting of a formyl, a carboxy, an optionally substituted alkoxycarbonyl, an optionally substituted aryloxycarbonyl, an optionally substituted carbamyl, an optionally substituted imine (—CH=NR$_a$), and an optionally substituted hydrazone (—CH=N—NHR$_b$), wherein $R_a$ and $R_b$ are independently selected from the group consisting of a hydrogen, an optionally substituted alkyl, an optionally substituted cycloalkyl, an optionally substituted arylalkyl, and an optionally substituted aryl, (iii) $R_3$ is selected from the group consisting of an ethenyl, a formyl, a carboxy, an optionally substituted alkoxycarbonyl, an optionally substituted aryloxycarbonyl, an optionally substituted carbamyl, and an optionally substituted ethyl (—CR$_c$R$_d$CR$_e$R$_f$R$_g$), wherein $R_c$, $R_d$, $R_e$, $R_f$, and $R_g$ are independently selected from the group consisting of a hydrogen, a halogen, and a hydroxyl, and (iv) $R_4$ is =O, =NR$_a$', or =N—NHR$_b$', wherein $R_a$' and $R_b$' are independently selected from the group consisting of a hydrogen, an optionally substituted alkyl, an optionally substituted cycloalkyl, an optionally substituted arylalkyl, and an optionally substituted aryl.

In one embodiment, $R_1$ is —COOCH$_3$.

In one embodiment, $R_2$ is a formyl.

In one embodiment, $R_3$ is an ethenyl.

In one embodiment, $R_4$ is =O.

In one embodiment, $R_5$ is —COOCH$_2$CH$_3$.

In one embodiment, the compound of formula (I) is

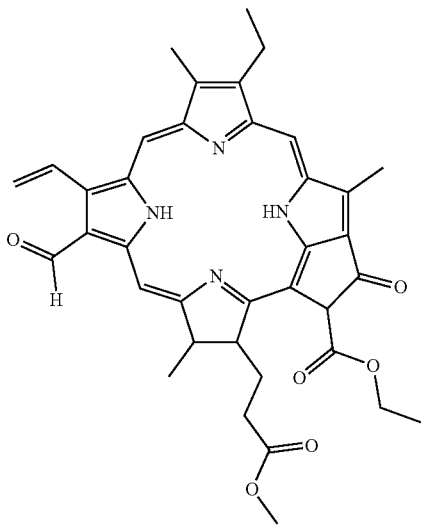

In one embodiment, the pharmaceutical composition contains 0.01-75 wt % of the compound of formula (I) relative to a total weight of the pharmaceutical composition.

In one embodiment, the exogenous pharmaceutically acceptable carrier and/or excipient is at least one selected from the group consisting of an organic solvent, a synthetic polymer, a synthetic fatty ester, and a surfactant.

In one embodiment, the exogenous pharmaceutically acceptable carrier and/or excipient is an organic solvent which is at least one selected from the group consisting of acetone, butanone, ethyl acetate, propyl acetate, dimethylformamide, dimethylacetamide, pyrrolidone, N-methyl-2-pyrrolidone, N-(2-hydroxyethyl) pyrrolidone, dimethyl sulfoxide, decylmethyl sulfoxide, tetradecylmethyl sulfoxide, methanol, ethanol, trifluoroethanol, n-propanol, i-propanol, n-butanol, i-butanol, t-butanol, propylene glycol, polyethylene glycol, and poly(tetramethylene ether) glycol.

In one embodiment, the exogenous pharmaceutically acceptable carrier and/or excipient is a synthetic polymer selected from the group consisting of a polylactide, a polyglycolide, a polycaprolactone, a polyanhydride, a polyurethane, a polyesteramide, a polyorthoester, a polydioxanone, a polyacetal, a polyketal, a polycarbonate, a polyorthocarbonate, a polyphosphazene, a polyhydroxybutyrate, a polyhydroxyvalerate, a polyalkylene oxalate, a polyalkylene succinate, a poly(malic acid), poly(maleic anhydride), a polyvinyl alcohol, a copolymer thereof, a terpolymer thereof, and combinations thereof.

According to a second aspect, the present disclosure relates to a method of treating a proliferative disorder. The method involves administering the pharmaceutical composition of the first aspect to a subject in need of therapy.

In one embodiment, the compound of formula (I) is

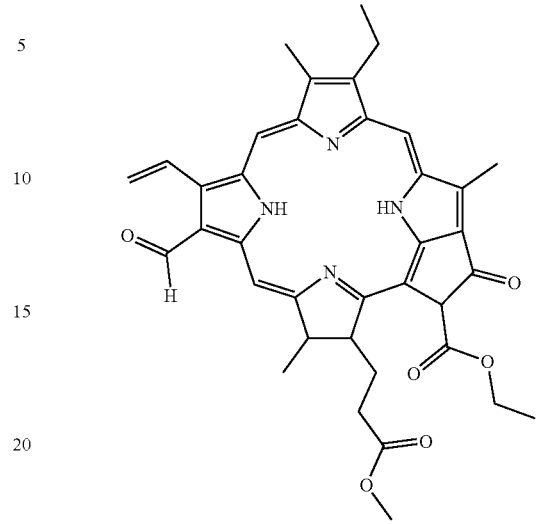

In one embodiment, the proliferative disorder is cancer.
In one embodiment, the cancer is at least one selected from the group consisting of leukemia, lymphoma, breast cancer, colon cancer, and prostate cancer.

In one embodiment, 0.1-500 mg/kg of the compound of formula (I) is administered per body weight of the subject.

According to a third aspect, the present disclosure relates to a method of isolating a compound from *Tecoma stans*. The method involves the steps of (i) mixing a *Tecoma stans* plant material with a first solution comprising a first alcohol to form an initial extract, (ii) mixing the initial extract with water and a first organic solvent to form a first aqueous layer and a first organic layer, (iii) concentrating the first organic layer to form a crude extract, (iv) mixing the crude extract with water, a second alcohol, and a second organic solvent to form a second aqueous layer and a second organic layer, (v) concentrating the second aqueous layer to form a residue comprising the compound, and (vi) isolating the compound, wherein the compound is

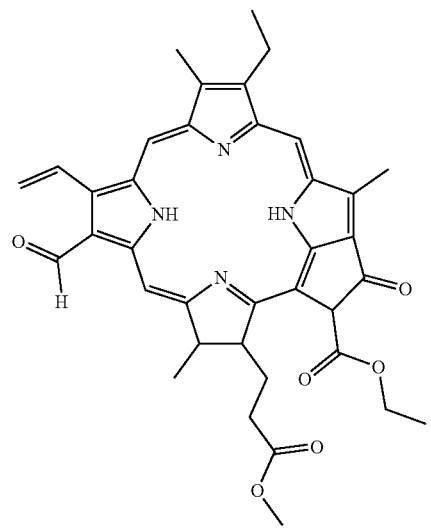

In one embodiment, the first organic solvent is a chlorinated solvent, and the second organic solvent is a non-polar solvent.

In one embodiment, the first alcohol is ethanol, and the second alcohol is methanol.

In one embodiment, the *Tecoma stans* plant material is sourced from leaves.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
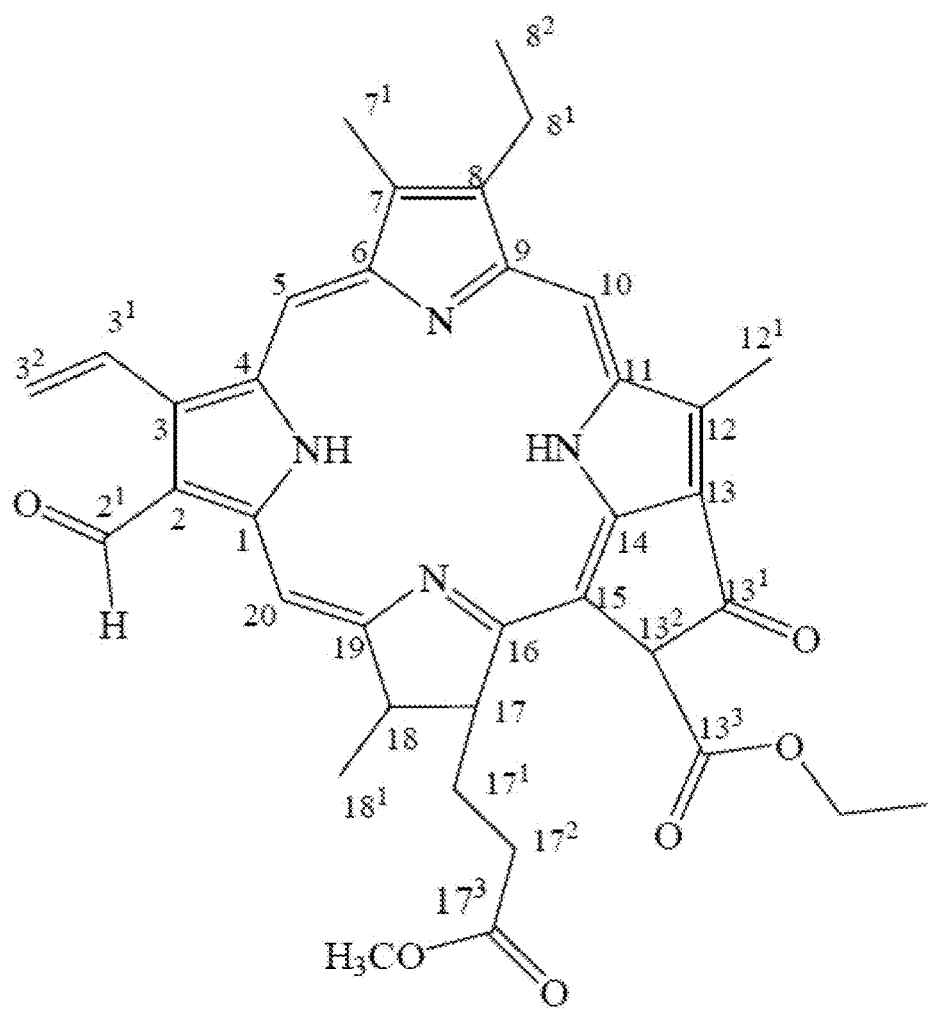
FIG. 1 shows the chemical structure of compound Tecomaphorbide derived from *Tecoma stans*.

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "compound" and "derivative" are used interchangeably, and are intended to refer to a chemical entity, whether in the solid, liquid or gaseous phase, and whether in a crude mixture or purified and isolated.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, and isotopes of oxygen include $^{16}O$, $^{17}O$ and $^{18}O$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

Although the open-ended term "comprising," as a synonym of terms such as including, containing, or having, is use herein to describe and claim the present composition and methods, the composition and/or methods may alternatively be described using more limiting terms, such as "consisting of" or "consisting essentially of" the recited ingredients/steps. For example, a pharmaceutical composition which consists essentially of the recited ingredients may contain other ingredients which do not adversely affect the anticancer and/or therapeutic properties of the composition. Although various illustrative embodiments are described herein, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether.

*Tecoma stans* (yellow bells, yellow trumpetbush) has sharply toothed, lanceolate shaped, pinnate green leaves and bears large, showy, bright golden yellow trumpet-shaped flowers. Common names for *Tecoma stans* plant include: yellow bells, ginger-thomas, trumpet flower, trumpet bush, yellow-elder, yellow trumpet bush, yellow trumpet flower(s), and tecoma. The plant grows well in warm climates. Traditionally, *Tecoma stans* is known for its antidiabetic effects and is widely used in south America, southeast Asia, and the east coast of the United States for treating diabetes. A concentrated decoction of the flowers and leaves of *Tecoma stans* may be taken orally as an antidiabetic medication.

A first aspect of the present disclosure relates to a method of isolating a compound having the following structure

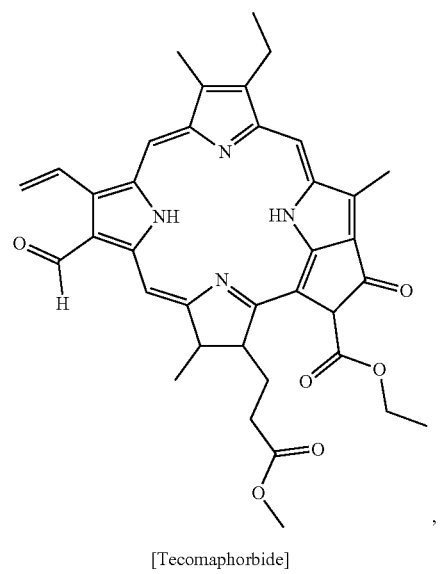 [SMILES: C=Cc1c(C=O)c2cc3nc(c4c5[nH]c(cc6nc(cc1[nH]2)C(C)=C6CC)c(C)c5C(=O)C4C(=O)OCC)C(CCC(=O)OC)C3C]

[Tecomaphorbide]

from a *Tecoma* plant, such as *Tecoma stans*. This compound, hereinafter referred to as "Tecomaphorbide", has not been reported before.

Other species of *Tecoma* that may be used in addition to or in lieu of *Tecoma stans* include, but are not limited to, *Tecoma beckii*, *Tecoma capensis*, *Tecoma castanifolia*, *Tecoma cochabambensis*, *Tecoma fulva*, *Tecoma nyassae*, *Tecoma rosifolia*, *Tecoma tenuiflora*, *Tecoma weberbaueriana*, and combinations thereof. Hybrid types such as *Tecoma×smithii* may be used as a species of *Tecoma*. A hybrid name contains "×" which links the parents of the hybrid.

As used herein, "plant" or "plant part" refers to any living organism of the kingdom Plantae and includes all plants described as grains, fruits and vegetables as well all plant parts or components including, but not limited to, roots, leaves, barks, branches, seeds, stems, stem shoots, bulbs, nuts, beans, grains, flowers, flower bud, pollen, vegetable skins, fruits and fruit skins during all periods of growth, preferably flowers, roots, barks, fruits, stems, and leaves during all periods of growth.

The *Tecoma stans* plant material used herein may be sourced from a whole plant, a leaf, a stem, a bark, a flower, a bud, a root, a fruit, pulp, or combinations thereof. Preferably, Tecomaphorbide is isolated from at least a part of a leaf of *Tecoma stans*. The *Tecoma stans* plant may be at any growth stage, e.g. at a flowering stage when the flower and/or one or more non-flower parts (e.g. leaf, stem, and root) may be used, or alternatively, at a non-flowering stage, when one or more non-flower parts may be used.

The plant part(s) of interest may be collected and then washed thoroughly, preferably twice/thrice with water, to remove both epiphytes and necrotic plants; preferably followed by washing with water to remove associated debris if any. In some embodiments, tap water, distilled water, doubly distilled water, deionized water, deionized distilled water, or combinations thereof may be used to wash the plant part(s) of interest. The water may be sterile. In one embodiment, the water may have a conductivity of less than 10 µS·cm-1, less than 5 µS·cm-1, or less than 1 µS·cm-1 at 20-30° C.; and/or a resistivity greater than 0.1 MΩ·cm, greater than 1 MΩ·cm, greater than 5 MΩ·cm, or greater than 10 MΩ·cm at 20-30° C.; and/or a total solid concentration less than 5 mg/kg, less than 1 mg/kg, or less than 0.5 mg/kg; and/or a total organic carbon concentration less than 1000 µg/L, less than 200 µg/L, or less than 50 µg/L. The clean and fresh plant part(s) may be sun-dried or dried in the shade/dark room for 5-60 days, preferably 10-45 days, more preferably 20-30 days, and then finely cut/chopped, or preferably ground/powdered/pulverized using, for example, a blender.

An initial extract of the *Tecoma stans* may be obtained by expression, fermentation, distillation, steam distillation, pressing, organic extraction, supercritical $CO_2$ extraction, or additional extraction methods known to those of ordinary skill in the art. For example, the initial extract may be obtained by extracting fresh/dried/ground plant part(s) of interest with supercritical $CO_2$ at a pressure of 140-300 bar, 180-250 bar, or 200-220 bar, at 50-80° C., or 55-70° C., for 30-240 minutes, 60-180 minutes, or 100-150 minutes. In a preferred embodiment, the initial extract of *Tecoma stans* is obtained by mixing the fresh/dried/ground plant part(s) of interest with a first solution comprising a first alcohol.

Exemplary alcohols applicable to the presently disclosed method include, but are not limited to, methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, and cyclohexanol. In a preferred embodiment, the first alcohol is ethanol. In one embodiment, an amount of the fresh/dried/ground plant part(s) may be 1-100 g/L, 5-50 g/L, 10-30 g/L, or about 20 g/L of the first alcohol.

Other solvents that may be used in addition to or in lieu of the alcohol for the initial extraction of *Tecoma stans* include, but are not limited to, ethers (e.g. diethyl ether, dibutyl ether, tetrahydrofuran, 1,4-dioxane, tetrahydropyran, t-butyl methyl ether, cyclopentyl methyl ether, di-iso-propyl ether), polyols (propylene glycol, polyethylene glycol, glycerol, poly(tetramethylene ether) glycol), aromatic solvents (e.g. benzene, o-xylene, m-xylene, p-xylene, and mixtures of xylenes, toluene, mesitylene, anisole, 1,2-dimethoxybenzene, α,α,α,-trifluoromethylbenzene, fluorobenzene), hydrocarbons (e.g., cyclohexane, n-hexane, isooctane, n-pentane), and chlorinated solvents (dichloromethane, chloroform, carbon tetrachloride, perchloroethylene (tetrachloroethylene), 1,1,2,2-tetrachloroethane, 1,1,2-trichloroethane, trichloroethylene, methyl chloroform (1,1,1-trichloroethane), 1,2,3-trichloropropane, ethylene dichloride, 1,2-dichloropropane (propylene dichloride), 1,2-dichloroethylene, 1,1-dichloroethane, chlorobenzene).

The fresh/dried/ground plant part(s) of interest may be mixed with the first alcohol (e.g. ethanol) for longer than 1 hour, 12 hours, or 24 hours, and up to 30 days, 20 days, or 10 days. The resulting mixture may be agitated for at least a part of the mixing duration using an agitator, a vortexer, a rotary shaker, a magnetic stirrer, a centrifugal mixer, and/or an overhead stirrer. In another embodiment, the resulting mixture is left to stand (i.e. not stirred). In one embodiment, the resulting mixture is sonicated in an ultrasonic bath or with an ultrasonic probe. The mixing may occur at a temperature in a range of 4-40° C., 10-30° C., or 15-28° C. Alternatively, the resulting mixture may be heated at a temperature of 40-70° C., 45-60° C., or 50-55° C. for at least a part of the mixing duration. An external heat source, such as a water bath or an oil bath, an oven, microwave, or a heating mantle, may be employed to heat the mixture. After the mixing process, the resulting mixture may be filtered until no insoluble material appears in the filtrate. The process of extraction may be carried out for up to 8 times, 5 times, or 3 times. For example, the residue collected from the filtration may be mixed with fresh batch of the first alcohol for subsequent rounds of extraction. The filtrate (or combined filtrates from several rounds of extraction) may be concentrated under a reduced pressure, thereby obtaining the initial extract.

Prior to the initial extraction, the fresh/dried/ground plant part(s) of interest may be submerged in a non-polar solvent including, but not limited to, petroleum ether, n-hexane, n-pentane, and n-heptane in order to remove/reduce fatty acids present in the plant. In a preferred embodiment, 1 kg of the fresh/dried/ground plant part(s) of interest is soaked in 1-100 L petroleum ether, preferably 5-50 L petroleum ether, more preferably 10-25 L petroleum ether. The soaking may be performed at a temperature of 4-60° C., 10-45°, or 20-35° C. for 1-30 days, 5-20 days, or 10-20 days.

The initial extract may be mixed with water and a first organic solvent using the agitation methods disclosed herein or by shaking a separatory funnel containing the initial extract, water and the first organic solvent. The first organic solvent of the disclosed method may be any of the organic solvent disclosed herein. Preferably, the first organic solvent used for extracting Tecomaphorbide from the initial extract has a low solubility in water, and a capability of extracting the Tecomaphorbide from the initial extract.

In one embodiment, the first organic solvent is a chlorinated solvent. Non-limiting examples of chlorinated solvent include dichloromethane (DCM), chloroform, carbon tetrachloride, perchloroethylene (i.e. tetrachloroethylene), 1,1,2, 2-tetrachloroethane, 1,1,2-trichloroethane, trichloroethylene, methyl chloroform (i.e. 1,1,1-trichloroethane), 1,2,3-trichloropropane, ethylene dichloride, 1,2-dichloropropane (i.e. propylene dichloride), 1,2-dichloroethylene, 1,1-dichloroethane, and chlorobenzene. In a preferred embodiment, the first organic solvent is chloroform. A volume ratio of the water to the first organic solvent (e.g. chloroform) may be in a range of 1:10 to 5:1, 1:8 to 3:1, 1:6 to 2:1, 1:5 to 1:1, or 1:4 to 1:2.

After mixing the initial extract with the water and the first organic solvent, the resulting mixture is allowed to stand for a sufficient period of time, e.g. at least 30 seconds, at least 1 minute, at least 3 minutes, at least 5 minutes, etc., for the complete separation of the first aqueous layer and the first organic layer. In another embodiment, the resulting mixture may be centrifuged for an effective period of time (e.g. at least 1 minute, at least 3 minutes, or at least 5 minutes, etc.) at an effective speed (e.g. 500-5,000 rpm, 1,000-3,000 rpm, or 1,500-2,000 rpm).

The first organic layer may be concentrated by boiling away the solvent or removing the solvent under reduced pressure (e.g., 10-500 mbar, 50-300 mbar, or 100-200 mbar), thereby forming a crude extract. Tecomaphorbide remains in the crude extract after the solvent is removed.

The crude extract may be mixed with water, a second alcohol, and a second organic solvent using the agitation methods disclosed herein or by shaking a separatory funnel containing the crude extract, water, the second alcohol, and the second organic solvent. The second alcohol used herein may be any of the alcohol solvents disclosed herein. In a preferred embodiment, the second alcohol is methanol. Preferably, the second organic solvent used herein has a low miscibility with water, and/or the second alcohol (e.g. methanol). In a preferred embodiment, the second organic solvent is a non-polar solvent. Exemplary non-polar solvents include, but are not limited to, n-hexane, n-pentane, cyclopentane, cyclohexane, n-heptane, benzene, toluene, and diethyl ether. Most preferably, the second organic solvent is n-hexane.

In one embodiment, a volume ratio of the water to the second alcohol (e.g. methanol) is in a range of 1:1 to 20:1, 2:1 to 18:1, 4:1 to 16:1, 8:1 to 14:1, 9:1 to 12:1, or about 10:1. In a related embodiment, a volume ratio of the second organic solvent (e.g. n-hexane) to a total volume of the water and the second alcohol (e.g. methanol) is in a range of 1:10 to 5:1, 1:8 to 3:1, 1:6 to 2:1, 1:5 to 1:1, or 1:4 to 1:2.

After mixing the crude extract with the water, the second alcohol, and the second organic solvent, the resulting mixture is allowed to stand for a sufficient period of time, e.g. at least 30 seconds, at least 1 minute, at least 3 minutes, at least 5 minutes, etc., for the complete formation of the second aqueous layer and the second organic layer. In another embodiment, the resulting mixture may be centrifuged under conditions specified previously. The second aqueous layer may be concentrated by boiling away the solvents or removing the solvents under reduced pressure (e.g., 10-500 mbar, 50-300 mbar, or 100-200 mbar), thereby forming a residue. Tecomaphorbide remains in the residue after the solvents are removed.

Tecomaphorbide may be isolated and purified from the residue by methods known to those of ordinary skill in the art such as distillation, crystallization, column chromatography, and high pressure liquid chromatography (HPLC) (normal phase or reversed phase). Preferred methods include, purifying the residue with column chromatography (with silica or alumina as the stationary phase), preparative thin layer chromatography, and recrystallization. In one embodiment, the residue is purified with a silica gel column.

A weight ratio of the residue to the alumina may be in a range of 1:1 to 1:40, 1:2 to 1:30, or 1:5 to 1:10. Isocratic or gradient elution may be used. A single organic solvent or a mixture of organic solvents may be used to elute Tecomaphorbide. For example, benzene only, and/or benzene/ethyl acetate may be used in succession. In a preferred embodiment, Tecomaphorbide is eluted with a mixture of benzene and ethyl acetate in a volume ratio of (benzene:ethyl acetate) about 1:100 to about 100:1, about 1:20 to about 20:1, about 1:10 to about 10:1, or 1:5 to about 5:1. Tecomaphorbide may be further purified by carrying out the process of column chromatography for up to 5 times, 3 times, or 2 times using suitable eluent(s) such as benzene, ethyl acetate, n-hexane, n-pentane, methylene chloride, chloroform, methanol, and acetone.

A second aspect of the present disclosure relates to a method of making derivatives of Tecomaphorbide. The ester groups, the carbonyl (aldehyde/ketone) groups, and the alkene group may undergo reactions as described hereinafter. The progress of the reactions may be monitored by methods known to those of ordinary skill in the art, such as thin layer chromatography (TLC), gas chromatography (GC), nuclear magnetic resonance (NMR), infrared spectroscopy (IR), and high pressure liquid chromatography (HPLC) combined with ultraviolet (UV) detection or mass spectroscopy (MS). The reaction product(s) may be isolated and purified by methods known to those of ordinary skill in the art, such as filtration through a celite containing cartridge, aqueous work-up, extraction with organic solvents, distillation, crystallization, column chromatography, and high pressure liquid chromatography (HPLC) on normal phase or reversed phase.

Hydrolysis of Ester Group(s)

The ester groups may be hydrolyzed with acids or bases to form the carboxy group (—COOH) or the carboxylate group (—COO$^-$), respectively. For example, Tecomaphorbide may be mixed with a mineral acid or an inorganic base in a protic solvent. Preferably, the protic solvent may be water, methanol, ethanol, or mixtures thereof. The concentration of Tecomaphorbide may range from 0.01-1 M, 0.1-0.8 M, or 0.3-0.5 M. The mineral acid or the inorganic base may be present in an amount ranging from 1-40 mol %, 5-30 mol %, or 10-20 mol %, based on a number of moles of Tecomaphorbide. The reaction mixture may be left to stand or agitated with the methods disclosed herein at 4-32° C., 10-30° C., or 24-28° C., or heated to 40-100° C., 50-90° C., or 60-80° C. using the methods disclosed herein. The reaction mixture may be agitated for 1-36 hours, 5-24 hours, or 12-18 hours, thereby hydrolyzing the ester group(s).

Transesterification of Ester Group(s)

Ester groups (—CO$_2$R$_m$) may undergo transesterification reaction with an alcohol (R$_n$OH), where —R$_m$ is chemically different from —R$_n$. For example, Tecomaphorbide may be mixed with an optionally substituted alkyl alcohol, or an optionally substituted aryl alcohol in the presence of a mineral acid and optionally a polar aprotic solvent. Exemplary alcohols include those described above and an optionally substituted phenol (e.g., phenol, catechol, hydroquinone, 2,6-dimethoxybenzoquinone, gallic acid, and salicylic acid). Preferably, the mineral acid is hydrochloric acid and/or the solvent (if present) is THF. The concentrations of Tecomaphorbide and the alcohol may independently range from 0.01-1 M, 0.1-0.8 M, or 0.3-0.5 M. An amount of the mineral acid may range from 1-20 mol %, 5-15 mol %, or 8-12 mol %, based on a number of moles of Tecomaphorbide. The reaction mixture may be left to stand or agitated with the methods disclosed herein at 10-35° C., 20-30° C., or 24-28° C., or heated to 40-100° C., 50-90° C., or 60-80° C. using the methods disclosed herein. The reaction mixture may be agitated for 1-36 hours, 5-24 hours, or 12-18 hours, thereby forming the transesterification reaction product.

Alternatively, the transesterification can be accomplished in two steps. The first step is a hydrolysis of the ester group(s) as described above or by methods known to those of ordinary skill in the art. The second step involves an esterification of the carboxy/carboxylate group with the optionally substituted alkyl alcohol or the optionally substituted aryl alcohol. The esterification method is known to those of ordinary skill in the art.

Transamidation of Ester Group(s)

The ester groups may undergo a transamidation reaction with an optionally substituted amine. For example, Tecomaphorbide may be mixed with an optionally substituted amine in the presence of a tert-butoxide and a polar protic solvent. Exemplary amines include those described above and primary amines (e.g., methylamine, ethylamine, propylamine, cyclobutylamine, cyclopentylamine). Exemplary tert-butoxides include, without limitation, potassium tert-butoxide, lithium tert-butoxide, sodium tert-butoxide, magnesium tert-butoxide, and barium tert-butoxide. The polar protic solvent is preferably water. In some embodiments, a polar aprotic solvent (e.g., THF) is present in addition to water. Concentrations of Tecomaphorbide, the optionally substituted amine, and the tert-butoxide in the reaction mixture may independently range from 0.01-1 M, 0.1-0.8 M, or 0.3-0.5 M. A mole ratio of Tecomaphorbide to the optionally substituted amine may range from 1:1 to 1:2, 1:1.01 to 1:1.5, or 1:1.1 to 1:1.2. A mole ratio of Tecomaphorbide to the tert-butoxide may range from 1:1 to 1:5, 1:1.5 to 1:3, or about 1:2. The reaction mixture may be left to stand or agitated with the methods disclosed herein at 4-32° C., 15-30° C., or 24-28° C., or heated to 40-65° C., 45-60° C., or 50-55° C. using the methods disclosed herein. The reaction mixture may be agitated for 5-120 minutes, 10-100 minutes, or 30-60 minutes, thereby forming the transamidation reaction product.

Alternatively, transamidation can be accomplished in two steps. The first step is a hydrolysis of the ester group(s) as described previously or by methods known to those of ordinary skill in the art. The second step involves an amide bond formation between the carboxy/carboxylate group and the optionally substituted amine using methods known to those of ordinary skill in the art.

Oxidation of Aldehyde to Carboxylic Acid

The aldehyde (i.e. formyl) group of Tecomaphorbide may undergo an oxidation reaction with water in the presence of an oxidant. For instance, Tecomaphorbide may be mixed with water and a suitable oxidizing agent including, but not limited to, hydrogen peroxide, silver oxide ($Ag_2O$), peroxy acetic acid ($CH_3CO_3H$), chromium(VI) compounds (e.g. $H_2CrO_4$, $CrO_3$, $Na_2CrO_4$, $K_2Cr_2O_7$, $BaCrO_4$), and permanganate salts (e.g. $KMnO_4$, $NaMnO_4$, $Ca(MnO_4)_2$, $NH_4MnO_4$). In one embodiment, the permanganate salts are excluded from being used as the oxidizing agent to avoid oxidization of the ketone group of Tecomaphorbide. Concentrations of Tecomaphorbide, the water, and the oxidizing agent in the reaction mixture may independently range from 0.01-1 M, 0.1-0.8 M, or 0.3-0.5 M. A mole ratio of Tecomaphorbide to the water may range from 1:1 to 1:4, 1:1.1 to 1:2, or 1:1.2 to 1:1.5. A mole ratio of Tecomaphorbide to the oxidizing agent may range from 1:1 to 1:5, 1:1.5 to 1:4, or 1:2 to 1:3. The reaction mixture may be left to stand or agitated with the methods disclosed herein at 4-32° C., 15-30° C., or 24-28° C., or heated to 40-80° C., 45-70° C., or 50-60° C. using the methods disclosed herein. The reaction mixture may be agitated for 5-120 minutes, 10-100 minutes, or 30-60 minutes, thereby forming a Tecomaphorbide derivative of formula (I) wherein $R_2$ is a carboxy. The carboxy group may be neutralized with a base (e.g. sodium hydroxide) to form a carboxylate.

The carboxy/carboxylate group obtained via the oxidation of aldehyde may be further subjected to (i) esterification reaction with an optionally substituted alkyl alcohol or the optionally substituted aryl alcohol, or (ii) amidation reaction with an optionally substituted amine, using reactions specified previously or methods known to those of ordinary skill in the art.

Protecting Groups for Carbonyls

The carbonyl moieties of Tecomaphorbide (e.g. aldehyde, ketone) may be optionally protected to avoid interference with modification reactions of ester and/or alkene groups. For example, the aldehyde and/or ketone group of Tecomaphorbide may react with an alcohol in the presence of an acid catalyst (e.g. p-toluenesulfonic acid, hydrochloric acid) to form an acetal. Exemplary alcohols include, but are not limited to, ethylene glycol, 1,3-propanediol, 2,2-dimethyl-1,3-propanediol, methanol, and ethanol. A mole ratio of Tecomaphorbide to the alcohol may range from 1:1 to 1:6, 1:2 to 1:5, or 1:3 to 1:4. The reaction mixture may be left to stand or agitated with the methods disclosed herein at 4-32° C., 15-30° C., or 24-28° C., or heated to 40-80° C., 45-70° C., or 50-60° C. using the methods disclosed herein. The reaction mixture may be agitated for 5-120 minutes, 10-100 minutes, or 30-60 minutes, thereby forming acetal(s) derived from the carbonyls of Tecomaphorbide. After modifications of ester and/or alkene groups complete, the carbonyls may be de-protected upon removal of the acetal(s) under acidic conditions.

Due to steric and electronic effects, aldehydes are generally more reactive than ketones. Accordingly, selective protection of aldehyde group of Tecomaphorbide may be implemented by using only about 1 equivalent of diol for acetal formation.

Reaction of Aldehyde/Ketone with Primary Amine

The aldehyde (i.e. formyl) and/or ketone group of Tecomaphorbide may react with a primary amine at a proper pH level to form imine functionality. For example, Tecomaphorbide may be mixed with a primary amine $NH_2R_a$ or $NH_2R_a'$, where $R_a$ and $R_a'$ are independently selected from the group consisting of a hydrogen, an optionally substituted alkyl, an optionally substituted cycloalkyl, an optionally substituted arylalkyl, and an optionally substituted aryl. Exemplary primary amines include, but are not limited to, ammonia, alkyl amines (e.g. ethylamine, isobutylamine, propylamine, cyclohexanemethylamine), cycloalkyl amines (e.g. cyclohexylamine, cyclopentylamine, cyclobutylamine, cycloheptylamine), arylalkyl amines (e.g. benzylamine, 4-methoxybenzylamine, 4-methylbenzylamine, 4-fluorobenzylamine, 4-chlorobenzylamine, phenethylamine), and aryl amines (e.g. aniline, p-toluidine, m-toluidine, p-anisidine, 4-ethoxyaniline, 4-fluoroaniline, 4-chloroaniline, 1-naphthylamine, 2-naphthylamine, 1-aminoanthracene). A mole ratio of Tecomaphorbide to the primary amine may range from 1:2 to 2:1, 1:1.5 to 1.5:1, or about 1:1. The reaction may be conducted in neat condition (i.e. solvent free) or in the presence of a solvent. Suitable solvents include, without limitation, DCM, acetonitrile, tetrahydrofuran (THF), and toluene. Concentrations of Tecomaphorbide and the primary amine in the reaction mixture may independently range from 0.01-1 M, 0.1-0.8 M, or 0.3-0.5 M. In one embodiment, the reaction mixture has a pH ranging from 4-9, 5-8, or 6-7. The reaction may further involve the use of azeotropic distillation and/or use of a dehydrating agent, such as molecular sieves, anhydrous magnesium sulfate, and anhydrous calcium sulfate. The reaction mixture may be left to stand or agitated with the methods disclosed herein at 4-32° C., 15-30° C., or 24-28° C., or heated to 40-80° C., 45-70° C., or 50-60° C. using the methods disclosed herein. The reaction mixture may be agitated for 0.5-48 hours, 1-24 hours, or 6-12 hours, thereby forming a Tecomaphorbide derivative of formula (I) wherein $R_2$ is an imine (—CH=$NR_a$), and/or $R_4$ is =$NR_a'$.

Because ketones are less reactive than aldehydes towards amines, selective imine formation of aldehyde or ketone may be implemented by (i) using only about 1 equivalent of the primary amine, which reacts more readily with the aldehyde group of Tecomaphorbide to form imine bond, or (ii) selectively protecting the aldehyde group using the methods disclosed herein prior to reacting the primary amine and the ketone group of Tecomaphorbide.

Reaction of Aldehyde/Ketone with Hydrazine

The aldehyde (i.e. formyl) and/or ketone group of Tecomaphorbide may react with a hydrazine at a proper pH level to form hydrazone functionality. For example, Tecomaphorbide may be mixed with an optionally substituted hydrazine $NH_2NHR_b$ or $NH_2NHR_b'$, where $R_b$ and $R_b'$ are independently selected from the group consisting of a hydrogen, an optionally substituted alkyl, an optionally substituted cycloalkyl, an optionally substituted arylalkyl, and an optionally substituted aryl. Exemplary applicable hydrazines include, but are not limited to, hydrazine ($NH_2NH_2$), alkyl hydrazines (e.g. methylhydrazine, ethylhydrazine, 1-isopropylhydrazine, butylhydrazine, tert-butylhydrazine, 2,2,2-trifluoroethylhydrazine, cyanoethylhydrazine, ethyl hydrazinoacetate), cycloalkyl hydrazines (e.g. cyclohexylhydrazine, cyclopentylhydrazine), arylalkyl hydrazines (e.g. benzylhydrazine, (3-methylbenzyl)hydrazine, (4-methylbenzyl)hydrazine, phenethylhydrazine, (3-chlorobenzyl)hydrazine, (2-thienylmethyl)hydrazine), and aryl hydrazines (e.g. phenylhydrazine, 4-isopropylphenylhydrazine, 2-(trifluoromethyl)phenylhydrazine, 3-chloro-4-fluorophenylhydrazine, 2-nitrophenylhydrazine, 4-cyanophenylhydrazine, 4-methoxyphenylhydrazine, 1-naphthalenyl hydrazine). A mole ratio of Tecomaphorbide to the hydrazine may range from 1:3 to 3:1, 1:2 to 2:1, or about 1:1. The reaction may be conducted in neat condition (i.e. solvent free) or in the presence of a solvent. Suitable solvents include, without limitation, DCM, acetonitrile, tetrahydrofuran (THF), and toluene. Concentrations of Tecomaphorbide and the hydrazine in the reaction mixture may independently range from 0.01-1 M, 0.1-0.8 M, or 0.3-0.5 M. In one embodiment, the reaction mixture has a pH ranging from 4-9, 5-8, or 6-7. The reaction mixture may be left to stand or agitated with the methods disclosed herein at 4-32° C., 15-30° C., or 24-28° C., or slightly heated to 35-60° C., 40-55° C., or 45-50° C. using the methods disclosed herein. The reaction mixture may be agitated for 0.5-48 hours, 1-24 hours, or 6-12 hours, thereby forming a Tecomaphorbide derivative of formula (I) wherein $R_2$ is a hydrazone (—CH=N—$NHR_b$), and/or $R_4$ is =N—$NHR_b'$.

Because ketones are less reactive than aldehydes towards hydrazines, selective hydrazone formation of aldehyde or ketone may be implemented by (i) using only about 1 equivalent of the hydrazine, which reacts more readily with the aldehyde group of Tecomaphorbide to form a hydrazine functionality, or (ii) selectively protecting the aldehyde group using the methods disclosed herein prior to reacting the hydrazine and the ketone group of Tecomaphorbide.

Modifications of Alkene

The alkene moiety of Tecomaphorbide may undergo several reactions such as ozonolysis, hydrogenation, hydroxylation, dihydroxylation, epoxidation, halogenation, and other addition reactions with HCl, HBr, and HI. Examples of the reaction procedures are described hereinafter.

Ozonolysis of Alkene

Tecomaphorbide may be dissolved in an aprotic organic solvent such as dichloromethane and acetone. The organic solvent may contain water in an amount up to 10 vol %, 7 vol %, or 5 vol %, based on a total volume of the organic solvent. A concentration of Tecomaphorbide may be 0.01-1 M, 0.1-0.8 M, or 0.3-0.5 M. Ozone may be bubbled into the reaction mixture containing Tecomaphorbide. Preferably, the reaction mixture is agitated by the methods disclosed herein such as using a magnetic stirrer. The reaction mixture may be agitated at −5° C. to 5° C., −4° C. to 4° C., or −1° C. to 1° C. for 1-12 hours, 2-8 hours, or 4-6 hours. The reaction mixture may be temperature-regulated to prevent overheating and/or evaporation, for example, by a thermostatted circulator, a water and/or ice bath with/without salt, or ice packs. After the agitation, dimethyl sulfide may be added to the reaction mixture, thereby forming a Tecomaphorbide derivative of formula (I) wherein $R_3$ is a formyl group.

The formyl group obtained from the ozonolysis step may be subjected to further modifications using methods described previously regarding reactions of aldehyde.

Hydrogenation of Alkene

Tecomaphorbide may be dissolved in an aprotic solvent (preferably ethyl acetate), thereby forming a solution with a concentration of Tecomaphorbide in a range of 0.01-1 M, 0.1-0.8 M, or 0.3-0.5 M. A catalyst (e.g., palladium on carbon) may be added to the solution in an amount of 1-30 wt %, 5-20 wt %, or 8-15 wt %, based on the weight of the Tecomaphorbide. Hydrogen gas may be bubbled into the reaction mixture. Alternatively, the reaction flask may be pressurized with hydrogen gas to a pressure of 2-10 bar, 3-8 bar, or 4-6 bar. Preferably, the reaction mixture is agitated by the methods disclosed herein or with a shaker hydrogenation apparatus for 0.5-30 hours, 4-20 hours, or 8-15 hours, thereby forming hydrogenated Tecomaphorbide.

Halogenation of Alkene

Tecomaphorbide may be mixed with halogens, such as chlorine ($Cl_2$), bromine ($Br_2$), and iodine ($I_2$), in the presence of a chlorinated solvent (e.g., chloroform). A concentration of Tecomaphorbide may be 0.01-1 M, 0.1-0.8 M, or 0.3-0.5 M. A concentration of bromine or iodine in the reaction mixture may be 0.2-10 M, 0.4-8 M, 0.6-6 M. A mole ratio of Tecomaphorbide to the bromine or iodine may be 1:2 to 1:10, 1:3 to 1:8, or 1:5 to 1:7. For the chlorination reaction, chlorine gas is bubbled into the reaction mixture. The reaction mixture may be irradiated with a light source such as a xenon lamp, a mercurial lamp, a metal halide lamp, a LED lamp, a LED chip, a solar simulator, and a halogen lamp, under agitation at 16-32° C., 20-30° C., or 24-28° C. Two or more light sources may be used. Sunlight may also be used as the light source. The irradiation source may be fitted with a filter to block or attenuate light with wavelengths longer than 400 nm. In some embodiments, the irradiation source is a flame, a lantern, a gas discharge lamp, an incandescent bulb, a laser, a fluorescent lamp, an electric arc, a cathode ray tube. Preferably the irradiation source may have a total power output of 50-1,000 W, preferably 100-750 W, more preferably 250-600 W, and may be positioned 5-30 cm, preferably 7-20 cm, more preferably 8-15 cm from the closest surface of the mixture. The mixture may be irradiated for at least 1 minute, at least 10 minutes, or at least 20 minutes, and not more than 600 minutes, not more than 300 minutes, or not more than 100 minutes. Alternatively, the reaction mixture may be heated to 40-60° C., 45-55° C., or 48-52° C. using the methods disclosed herein, thereby forming halogenated Tecomaphorbide.

Hydroxylation of Alkene

Tecomaphorbide may be mixed with borane complexed with THF (borane.THF) in the presence of a dried aprotic solvent such as THF. The mixture may be left to stand or agitated at −5° C. to 5° C., −3° C. to 3° C., or −1° C. to 1° C. for 1-10 hours, 2-7 hours, or 4-6 hours. The mixture may be temperature-regulated to prevent overheating and/or evaporation using the methods described above. After which, a solution containing an inorganic base (e.g., sodium hydroxide) and a solution containing hydrogen peroxide may be added to the mixture. In the resulting reaction mixture, concentrations of Tecomaphorbide and borane THF may independently be 0.01-1 M, 0.1-0.8 M, or 0.3-0.5 M. A concentration of the solution containing the inorganic base may range from 0.5-5 M, 1-4 M, or 2-3 M. A concentration of the hydrogen peroxide solution may be 10-50 wt %, 20-40 wt %, or 25-35 wt %, based on a total weight of the hydrogen peroxide solution. A mole ratio of Tecomaphorbide to borane-THF may be 1:1 to 1:2, 1:1.01 to 1:1.3, or 1:1.02 to 1:1.1. A mole ratio of the solution containing the inorganic base to Tecomaphorbide may be 1:1 to 1:3, 1:1.01 to 1:1.5, or 1:1.02 to 1:1.2. A mole ratio of the solution containing hydrogen peroxide to Tecomaphorbide may be 1:1 to 1:4, 1:1.01 to 1:2, or 1:1.02 to 1:1.5. The reaction mixture is heated to 40-70° C., 45-65° C., or 50-60° C. for 10-120 minutes, 30-100 minutes, or 40-60 minutes, thereby forming the hydroxylation reaction product.

Dihydroxylation of Alkene

Tecomaphorbide may be mixed with hydrogen peroxide, and a catalyst, such as osmium tetroxide, vanadium oxide, or chromium oxide, in a solvent. The solvent may contain an alcohol, such as tert-butanol, and water. A concentration of Tecomaphorbide may be 0.01-5 M, 0.1-4 M, or 0.5-2 M. A concentration of hydrogen peroxide in the reaction mixture may be 0.01-15 M, 0.5-12 M, 2-9 M. A mole ratio of the Tecomaphorbide to hydrogen peroxide may range from 1:1 to 1:3, 1:1.1 to 1:2, or about 1:1.5. An amount of the catalyst may be 0.1-1 mol %, 0.2-0.7 mol %, or 0.3-0.5 mol % of the number of moles of the Tecomaphorbide. The resulting reaction mixture is then stirred at −5° C. to 5° C., −3° C. to 3° C., or −1° C. to 1° C. for 5-60 hours, 10-50 hours, or 30-40 hours, thereby forming dihydroxylated Tecomaphorbide. The reaction mixture may be temperature-regulated to prevent overheating and/or evaporation, for example, by a thermostatted circulator, a water and/or ice bath with/without salt, or ice packs.

A third aspect of the present disclosure relates to a pharmaceutical composition comprising or consisting essentially of a compound of formula (I)

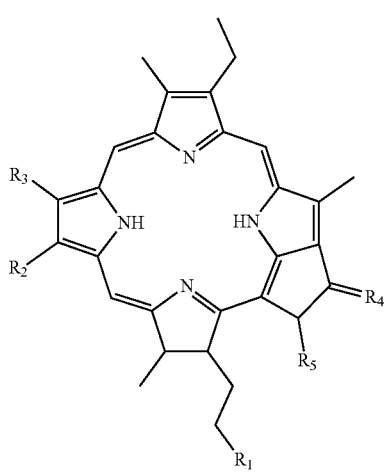

(I)

or a salt thereof, a solvate thereof, a tautomer thereof, a stereoisomer thereof, or a mixture thereof, and an exogenous pharmaceutically acceptable carrier and/or excipient which is not present in *Tacoma stans*.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers.

Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "alkenyl" refers to a straight, branched, or cyclic hydrocarbon fragment containing at least one C=C double bond. Exemplary alkenyl groups include, but are not limited to, ethenyl, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, cyclohexenyl, and the like.

The term "aryl", as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, stearoyl.

The term "aroyl" as used in this disclosure refers to an arylalkyl group with an alkyl carbon atom bound with a double bond to an oxygen atom and the alkyl carbon atom is adjacent to a ring carbon atom. Examples of aroyl are benzoyl and naphthoyl, and "substituted aroyl" may refer to benzoyl or naphthoyl substituted by at least one substituent including those selected from halogen, amino, vitro, hydroxy, alkyl, alkoxy and haloalkyl on the benzene or naphthalene ring.

The terms "alkoxy" and "alkyloxy" refer to a straight or branched alkyl group attached to an oxygen atom. Exemplary alkyloxy groups include, but are not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "alkoxycarbonyl" as used in this disclosure refers to an alkoxy group or a cycloalkyloxy group bound to a carbonyl group (i.e., C=O). Exemplary cycloalkyloxy groups are described hereinafter.

The term "aryloxycarbonyl" as used in this disclosure refers to an aryloxy group bound to a carbonyl group (i.e., C=O). Exemplary aryloxy groups are described hereinafter.

The term "carbamyl", as used herein, and unless otherwise specified, refers to an amide (—C(O)NR$_x$R$_y$) that is unsubstituted (—C(O)NH$_2$), monosubstituted (where R$_x$ is a hydrogen, R$_y$ is an optionally substituted alkyl, an optionally substituted cycloalkyl, an optionally substituted arylalkyl, or an optionally substituted aryl), or disubstituted where R$_x$ and R$_y$ are independently an optionally substituted alkyl, an optionally substituted cycloalkyl, an optionally substituted arylalkyl, or an optionally substituted aryl.

As used herein, the term "substituted" refers to compounds where at least one hydrogen atom is replaced with a non-hydrogen group, provided that normal valencies are maintained and that the substitution results in a stable compound. When a compound or a R group (denoted as $R_1$, $R_2$, and so forth) is noted as "optionally substituted", the substituents are selected from the exemplary group including, but not limited to, aroyl, halogen (e.g. chlorine, bromine, fluorine or iodine), alkyl, alkoxy, cycloalkyloxy (e.g., cyclopentyloxy, cyclohexyloxy, and cycloheptyloxy), aryloxy including phenoxy and phenoxy substituted with halo, alkyl, alkoxy, and haloalkyl which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl), hydrocarbyl, substituted hydrocarbyl, arylalkyl, hydroxy, oxo, alkanoyl, alkanoyloxy, amino, alkylamino, arylamino, arylalkylamino, disubstituted amines (e.g. in which the two amino substituents are selected from the exemplary group including, but not limited to, alkyl, aryl, or arylalkyl), alkanyl amino, aryl amino, alkanoyl amino, substituted alkanoyl amino, substituted aryl amino, thiol, alkylthio, arylthio, arylalkylthio, alkylthiono, arylthiono, aryalkylthiono, alkylsulfonyl, aryl sulfonyl, arylalkylsulfonyl, sulfonamido (e.g., —$SO_2NH_2$), substituted sulfonamide (e.g., —$SO_2$NHalkyl, —$SO_2$NHaryl, —$SO_2$NHarylalkyl or in cases where there are two substituents on the nitrogen, each substituent is independently an alkyl, an aryl, or an arylalkyl), nitro, cyano, carboxy, carbamyl (e.g. —$CONH_2$), substituted carbamyl, alkoxycarbonyl, aryl, substituted aryl, guanidine, heteroarylcarbonyl, substituted heteroarylcarbonyl, heterocyclyl, substituted heterocyclyl and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

$R_1$ and $R_5$ are independently selected from the group consisting of an optionally substituted alkoxycarbonyl, an optionally substituted aryloxycarbonyl, a carboxy, and an optionally substituted carbamyl, with the proviso that $R_1$ is neither —$COO(CH_2)_{19}CH_3$, nor —$COOCH_2$—CH=C($CH_3$)—$(CH_2)_3$CH($CH_3$)—$(CH_2)_3$CH($CH_3$)—$(CH_2)_3$CH($CH_3$)$_2$. In one embodiment, $R_1$ is an optionally substituted alkoxycarbonyl. Preferably, $R_1$ is —$COOCH_3$. In one embodiment, $R_5$ is an optionally substituted alkoxycarbonyl. Preferably, $R_5$ is —$COOCH_2CH_3$.

$R_2$ is selected from the group consisting of a formyl, a carboxy, an optionally substituted alkoxycarbonyl, an optionally substituted aryloxycarbonyl, an optionally substituted carbamyl, an optionally substituted imine (—CH=$NR_a$), and an optionally substituted hydrazone (—CH=N—$NHR_b$), wherein $R_a$ and $R_b$ are independently selected from the group consisting of a hydrogen, an optionally substituted alkyl, an optionally substituted cycloalkyl, an optionally substituted arylalkyl, and an optionally substituted aryl. In a preferred embodiment, $R_2$ is a formyl.

$R_3$ is selected from the group consisting of an ethenyl, a formyl, a carboxy, an optionally substituted alkoxycarbonyl, an optionally substituted aryloxycarbonyl, an optionally substituted carbamyl, and an optionally substituted ethyl (—$CR_cR_dCR_eR_fR_g$), wherein $R_c$, $R_d$, $R_e$, $R_f$, and $R_g$ are independently selected from the group consisting of a hydrogen, a halogen, and a hydroxy. In a preferred embodiment, $R_3$ is an ethenyl.

$R_4$ is =O, =$NR_a'$, or =N—$NHR_b'$, wherein $R_a'$ and $R_b'$ are independently selected from the group consisting of a hydrogen, an optionally substituted alkyl, an optionally substituted cycloalkyl, an optionally substituted arylalkyl, and an optionally substituted aryl. In a preferred embodiment, $R_4$ is =O.

The present disclosure is intended to include metalation product of formula (II) derived from the compound of formula (I).

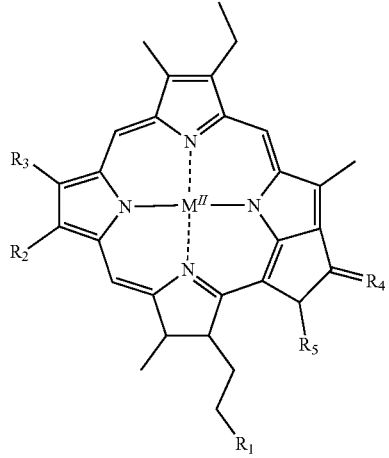

(II)

wherein $R_1$, $R_2$, $R_3$, $R_4$, and $R_5$ are as previously specified, with the proviso that $R_1$ is neither —$COO(CH_2)_{19}CH_3$, nor —$COOCH_2$—CH=C($CH_3$)—$(CH_2)_3$CH($CH_3$)—$(CH_2)_3$CH($CH_3$)—$(CH_2)_3$CH($CH_3$)$_2$ (i.e. —COO-Phytyl), and M is a metal selected from the group consisting of Mg, Mn, Fe, Cu, Co, Ni, and Zn. The metalation product may be prepared by metalation or transmetallation methods known to those of ordinary skill in the art, such as mixing a desirable compound of formula (I) with a metal salt M(II) in the presence of a solvent (e.g. DCM, DMF, THF) under basic condition with a pH ranging from 8-13, 9-12, or 10-11. The resulting metalation product can be obtained, for example, by precipitation, and washing with a solvent (e.g. diethyl ether), and purified as needed.

In a preferred embodiment, the compound of formula (I) is

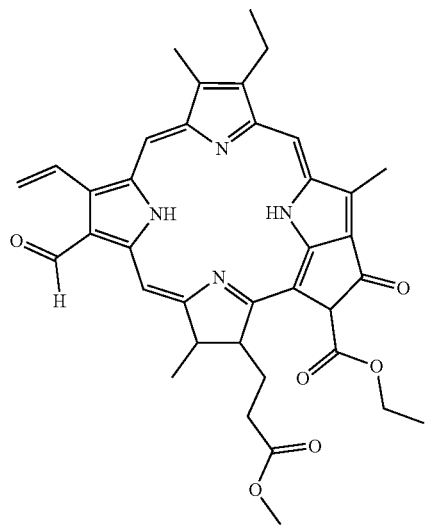

[Tecomaphorbide]

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, a compound represented by formula (I), a salt thereof, a solvate thereof, a tautomer thereof, a stereoisomer thereof, a compound represented by formula (II), a salt thereof, a solvate thereof, a tautomer thereof, a stereoisomer thereof, or any mixtures of these compounds. In some embodiments, other active ingredients in addition to the compound of the current disclosure may be incorporated into the pharmaceutical composition.

In one or more embodiments, the compound of the pharmaceutical composition disclosed herein is

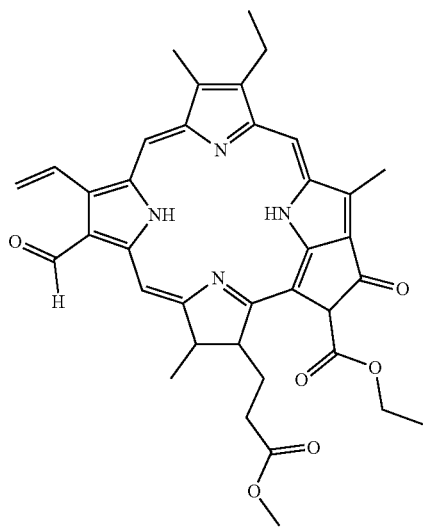

[Tecomaphorbide]

In one embodiment, the pharmaceutical composition contains 0.01-75 wt % of the compound disclosed herein in any of its embodiments relative to a total weight of the pharmaceutical composition. In preferred embodiments, the pharmaceutical composition comprises at least 0.001 wt %, at least 0.01 wt %, at least 0.1 wt %, at least 0.5 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 99 wt %, or at least 99.9 wt % of the compound relative to a total weight of the pharmaceutical composition. The pharmaceutical composition may contain 0.05-500 µM of the compound relative to a total volume of the composition, preferably 0.5-400 µM, preferably 5-300 µM, preferably 10-200 µM, preferably 50-100 µM of the compound relative to the total volume of the composition. In some embodiments, the composition comprises up to 0.1 wt %, up to 1 wt %, up to 5 wt %, up to 10 wt %, up to 25 wt %, or up to 50 wt % of a pharmaceutically acceptable salt of the compound. In some embodiments, the composition comprises up to 0.1 wt %, 1 wt %, 10 wt %, or 50 wt % of a pharmaceutically acceptable solvate of the compound. In one or more embodiments, the pharmaceutical composition comprises up to 0.01%, up to 0.1%, up to 1%, up to 5%, up to 10%, or up to 25% by weight of the pharmaceutically acceptable carrier and/or excipient relative to a total weight of the pharmaceutical composition. Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

In some embodiments, the active ingredient of the current disclosure, e.g. a compound represented by formula (I), a salt thereof, a solvate thereof, a tautomer thereof, a stereoisomer thereof, a compound represented by formula (II), a salt thereof, a solvate thereof, a tautomer thereof, a stereoisomer thereof, or any mixtures of these compounds, provides utility as an anticancer agent in reducing the viability of cancer cells derived from human cancer cell lines including, but not limited to, leukemia cell lines (e.g. HL-60, MOLM-13, MOLM-14, MV4-11, Jurkat cells, K562), lymphoma cell lines (e.g. U937, SU-DHL-1, MC116), breast cancer cell lines (e.g. MCF7, SK-BR-3), colon cancer cell lines (e.g. Caco-2, HCT-116, HT-29), prostate cancer cell lines (e.g. PC-3), stomach cancer cell lines (e.g. N87, SNU-16), liver cancer cell lines (e.g. HepG2), lung cancer cell lines (e.g. A549, NCI-H460), brain tumor cell lines (e.g. U251), ovarian cancer cell lines (e.g. NCI-ADR/RES, OVCAR-03), renal cancer cell lines (e.g. 786-0), and melanoma cell lines (e.g. UACC-62).

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis. The active ingredient of the present disclosure may also exhibit other therapeutic activities such as antimicrobial (e.g. antibacterial, antifungal, antiviral, antimycobacterial), antimalarial, pesticidal, antioxidant, as well as anti-inflammatory efficacies.

For example, the active ingredient (e.g. Tecomaphorbide) may be useful for treating skin diseases or conditions such as warts, corns, calluses, and umbilical granulomas, melanoma, basal cell carcinoma (BCC), psoriasis, viral infection caused by the herpes simplex virus (e.g. cold sores), nail deformations (e.g. ingrown toenails), mouth ulcers (canker sores), ichthyoses, porokeratoses, follicular keratoses, palmoplantar keratodermas, eczema, acne, dandruff, and dry skin.

In some embodiments, the ability of the active ingredient to reduce the viability of cancer cells may be determined by contacting the pharmaceutical composition with the cancer cells and then performing cell viability assays. Methods of such assays include, but are not limited to, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, sulforhodamine B (SRB) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, leukemia cell lines, e.g., HL-60, MOLM-13, MOLM-14, MV4-11, Jurkat cells, K562, CESS, CCRF-CEM, CEM/C1, KASUMI-1, and ARH-77, lymphoma cell lines, e.g. U937, TUR, SU-DHL-1, SU-DHL-8, and MC116, breast cancer cell lines, e.g., MDA-MB-231, MCF-7, T47D, and VP303, colon cancer cell lines, e.g., HCT15, MDST8, GP5d, HCT116, DLD1, HT29, SW620, SW403, and T84, prostate cancer cell lines, e.g., Caco-2, PC3, VCaP, C4-2B, and MDA PCa 2b, stomach cancer cell lines, e.g., N87, SNU-16, SNU-5, SNU-1, KATO III, AGS, liver cancer cell lines, e.g. HepG2, PLC/PRF/5, THLE-3, C3A, SNU-182, SNU-398, SNU-387, SNU-423, SNU-475, SNU-449, and Hep 3B2.1-7, lung cancer cell lines, e.g., A549, SHP-77, COR-L23/R, and NCI-H69/LX20, cervical cancer cell Lines, e.g., HeLa DH, HtTA-1, HRS, and C-41, ovarian cancer cell lines, e.g., A2780, A2780cis, OV7, and PE023, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably leukemia, lymphoma, breast cancer, colon cancer, and/or prostate cancer.

In some embodiments, the active ingredient (e.g. "Tecomaphorbide") may be selective toward cancer cells and is non-toxic toward normal (i.e., non-cancerous) cells. In the context of the disclosure, the term "non-toxic" means that the active ingredient does not inhibit the proliferation of the normal cells. Exemplary normal cells include, without limitation, human primary T-cells (see FIG. 2), primary epidermal keratinocytes, primary gingival keratinocytes, primary bladder epithelial cells, primary bronchial/tracheal epithelial cells, and primary mammary epithelial cells. The primary cells may be obtained from the American Type Culture Collection (ATCC).

As used herein, the term "cytotoxic effective amount" refers to a concentration of the active ingredient that reduces the viability of the cancer cells by at least 5%, at least 10%, at least 15%, at least 20%, at least 30%, at least 40%, at least 50%, at least 60%, at least 70%, at least 80% or at least 90%, relative to cancer cells not treated with the active ingredient. The reduction in viability may occur no more than 10 days, no more than 7 days, no more than 5 days, no more than 3 days, or no more than 2 days after the active ingredient is contacted with the cancer cells. In one embodiment, the cytotoxic effective amount may be the $IC_{50}$ which is a concentration of the active ingredient which causes the death of 50% of cancer cells in 6-72 hours, 10-48 hours, or about 12 hours.

In one embodiment, the $IC_{50}$ of the presently disclosed compounds (e.g. Tecomaphorbide) against leukemia cells (e.g. 1-L-60, MOLM-13, MV4-11, Jurkat cells, K562) is in a range of 0.2-1.7 µM, preferably 0.4-1.2 µM, more preferably 0.6-0.9 µM. In another embodiment, the $IC_{50}$ of the presently disclosed compounds (e.g. Tecomaphorbide) against lymphoma cells (e.g. U937) is in a range of 0.7-1.8 µM, preferably 0.9-1.5 µM, more preferably 1.1-1.3 µM. In another embodiment, the $IC_{50}$ of the presently disclosed compounds (e.g. Tecomaphorbide) against breast cancer cells (e.g. MCF-7) is in a range of 1.5-3.1 µM, preferably 1.8-2.7 µM, more preferably 2.0-2.4 µM. In another embodiment, the $IC_{50}$ of the presently disclosed compounds (e.g. Tecomaphorbide) against colon cancer cells (e.g. Caco-2) is in a range of 1.8-3.6 µM, preferably 2.2-3.2 µM, more preferably 2.4-2.8 µM. In another embodiment, the $IC_{50}$ of the presently disclosed compounds (e.g. Tecomaphorbide) against prostate cancer cells (e.g. PC-3) is in a range of 1.4-2.5 µM, preferably 1.5-2.2 µM, more preferably 1.7-1.9 µM (see Table 2 of Example 5).

In some embodiments, other active ingredients in addition to the compound(s) of the current disclosure may be incorporated into the pharmaceutical composition. In one embodiment, the pharmaceutical composition includes a second active ingredient that is chemically distinct from the compounds of formulae (I), and (II), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The composition may contain 0.1-50 wt % of the chemotherapeutic agent, preferably 10-40 wt %, more preferably 10-20 wt %, relative to the weight of the active ingredient. In one embodiment, the chemotherapeutic agent is at least one of a mitotic inhibitor; an alkylating agent; an antimetabolite; a cell cycle inhibitor; an enzyme; a topoisomerase inhibitor such as CAMPTOSAR (irinotecan); a biological response modifier; an anti-hormone; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; methylhydrazine derivative, e.g., procarbazine; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Examples of alkylating agents include, without limitation, fluorouracil (5-FU) alone or in further combination with leukovorin; other pyrimidine analogs such as UFT, capecitabine, gemcitabine and cytarabine; the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents include, without limitation, folic acid analogs, e.g., methotrexate (used in the treatment of acute lymphocytic leukemia, choriocarcinoma, mycosis fungoides, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx, CELEBREX (celecoxib), valdecoxib, paracoxib, rofecoxib, and COX 189.

Some examples of MMP inhibitors useful are AG-3340, RO 32-3555, RS 13-0830, and compounds such as 3-[[4-(4-fluorophenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1] octane-3-carboxylic acid hydroxyamide; (2R,3R) 1-[4-(2-chloro-4-fluoro-benzyloxy)-benzenesulfonyl]-3-hydroxy-3-methylpiperidine-2-carboxylic acid hydroxyamide; 4-[4-(4-fluorophenoxy)-benzenesulfonylamino]-tetrahydro-pyran-4-carboxylic acid hydroxyamide; 3-[[4-(4-fluoro-phenoxy) benzenesulfonyl]-(1-hydroxycarbamoyl-cyclobutyl)-amino]-propionic acid; 4-[4-(4-chloro-phenoxy) benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluorophenoxy)-benzenesulfonylamino]-8-oxa-bicyclo [3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

The pharmaceutical composition may comprise other chemotherapeutic agents, including, but not limited to, agents capable of enhancing antitumor immune responses, such as CTLA4 (cytotoxic lymphocite antigen 4) antibodies, other agents capable of blocking CTLA4, trastuzumab, cetuximab, panitumumab, rituximab, bevacizumab, mapatumumab, conatumumab, and lexatumumab.

The active ingredient can be used in combination with one or more other chemotherapeutic agents. The dosage of the active ingredient and/or the chemotherapeutic agent may be adjusted for any drug-drug reaction.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

The exogenous pharmaceutically acceptable carrier and/or excipient may be at least one selected from the group consisting of an organic solvent, a synthetic polymer, a synthetic fatty ester, and a surfactant. The following carriers and excipients are not present in *Tacoma stans*.

Exemplary organic solvents include, but are not limited to, the organic solvents and organic acids described herein in addition to glycol ethers (e.g. 1,2-dimethoxyethane, diglyme, triglyme), alkyl methyl sulfoxide (e.g., dimethyl sulfoxide, decylmethyl sulfoxide, tetradecylmethyl sulfoxide), ketone (e.g., acetone, butanone), esters (e.g. ethyl acetate, propyl acetate), an amide/lactam (e.g. dimethylformamide, dimethylacetamide, pyrrolidone, N-methyl-2-pyrrolidone, N-(2-hydroxyethyl) pyrrolidone), acetonitrile, propionitrile, butyronitrile, benzonitrile, ethylene carbonate, propylene carbonate, 1,3-dimethyl-3,4,5,6-tetrahydro-2 (1H)-pyrimidinone, and mixtures thereof.

Exemplary synthetic polymers include, but are not limited to, polylactides, polyglycolides, polycaprolactones, polyanhydrides, polyurethanes, polyesteramides, polyorthoesters, polydioxanones, polyacetal s, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to an monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethylammonium chloride, and dodecylammonium chloride, and combinations thereof.

In some embodiment, the exogenous pharmaceutically acceptable carrier and/or excipient contains a fatty acid, a vegetable oil, or both, and a weight ratio of the compound of formula (I) to a total weight of the fatty acid, the vegetable oil, or both ranges from 1:4 to 10:1, preferably 1:3 to 8:1, preferably 1:2 to 6:1, preferably 1:1 to 5:1, preferably 2:1 to 4:1.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, peanut oil, grape seed oil, hazelnut oil, linseed oil, rice bran oil, safflower oil, sesame oil, brazil nut oil, carapa oil, passion fruit oil, and cocoa butter.

Depending on the route of administration e.g. oral, parental, or topical, the pharmaceutical composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices.

Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the presently disclosed compound(s), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to a fourth aspect, the present disclosure relates to a method for treating a proliferative disorder, preferably cancer. The method involves administering the pharmaceutical composition of the third aspect to a subject in need of therapy.

In one or more embodiments, the disclosed method of the current aspect is for treating cancer of the blood, stomach, breast, colon, brain, bladder, lung, cervix, ovary, rectum, pancreas, skin, prostate gland, spleen, liver, kidney, head, neck, testicle, bone, bone marrow, thyroid gland, or central nervous system. In preferred embodiments, the cancer is at least one selected from the group consisting of leukemia, lymphoma, breast cancer, colon cancer, and prostate cancer.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had chemotherapy and radiation therapy for other cancers, (ii) has genetic disorders, such as Down syndrome, and/or (iii) exposure to certain chemicals, such as benzene are at a higher risk of contracting leukemia. People who (i) have immune system diseases or take Immunosuppressant drugs, (ii) have been infected with Epstein-Barr virus or *Helicobacter pylori*, and/or (iii) were exposed to chemicals such as benzene are at a higher risk of contracting lymphoma. Women who have (i) certain inherited genes (e.g. mutated BRCA1 and/or mutated BRCA2), (ii) been taking estrogen alone (without progesterone) after menopause for many years (at least 5, at least 7, or at least 10), and/or (iii) been taking fertility drug clomiphene citrate are at a higher risk of contracting breast cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. People who (i) have certain inherited mutated genes (e.g. mutated RNASEL, mutated BRCA1 and/or mutated BRCA2), (ii) had inflammation in the prostate, and/or (iii) are obese are at a higher risk of contracting prostate cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In a preferred embodiment, the active ingredient and/or the pharmaceutical composition described herein are administered orally.

In one embodiment, the pharmaceutical composition administered comprises a compound of formula (I), a salt thereof, a solvate thereof, a tautomer thereof, a stereoisomer thereof, a compound of formula (II), a salt thereof, a solvate thereof, a tautomer thereof, a stereoisomer thereof, or any mixtures of these compounds. In a preferred embodiment, the pharmaceutical composition contains a compound of formula (I) which is

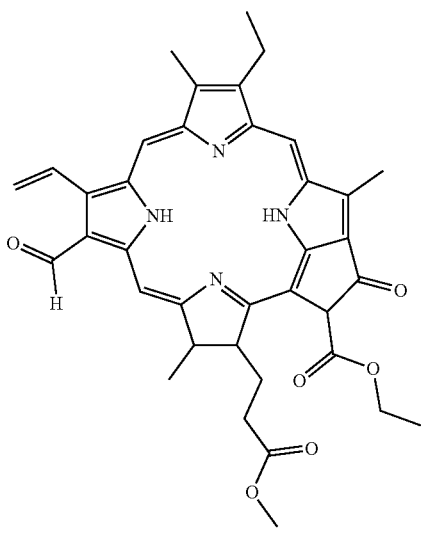

[Tecomaphorbide]

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In one or more embodiments, an effective amount of the compound disclosed herein in a range of 0.1-500 mg/kg, preferably 1-200 mg/kg, more preferably 10-50 mg/kg is administered per body weight of the subject. However, in certain embodiments, the effective amount of the compound is less than 0.1 mg/kg or greater than 500 mg/kg.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be performed before or after the pharmaceutical composition is administered.

A treatment method may comprise administering a pharmaceutical composition containing the compound of the current disclosure in any of its embodiments as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In certain embodiments, the composition and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In one embodiment, the method disclosed herein may reduce the number of abnormal peripheral blood mononuclear cells in a leukemia patient, who may be afflicted with acute lymphoblastic leukemia (ALL) (e.g. T-cell acute lymphoblastic leukemia), acute myeloid leukemia (AML) (e.g. acute promyelocytic leukemia (APL), acute monocytic leukemia (AmoL)), biphenotypic B myelomonocytic leukemia, chronic lymphocytic leukemia (CLL), or chronic myeloid leukemia (CML, or chronic myelogenous leukemia). Preferably, the number of abnormal peripheral blood mononuclear cells is reduced after the treatment by at least 5%, at least 10%, at least 20%, at least 30%, or at least 40%, and up to 100%, up to 99%, up to 95%, up to 90%, up to 80%, or up to 60%, relative to an initial number of abnormal peripheral blood mononuclear cells before treatment.

In most embodiments, the method further comprises measuring a concentration of a biomarker and/or detecting a mutation in a biomarker before and/or after the pharmaceutical composition comprising the compound of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC).

Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin Dl, cyclin E, and ERI3. Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for prostate cancer include, without limitation, tPSA, fPSA, p2PSA, HOXC6 DLX1, GSTP1, RASSF1, and APC. Exemplary biomarkers for lymphoma include, without limitation, B-cell lymphoma 6 (BCL6), B-cell lymphoma 2 (BCL2), tumor protein 53 (TP53), MYD88, MYC, SPIB, TNFAIP3, and CIITA. In one embodiment, leukemia patient's response to the treatment may be monitored by (i) measuring the complete blood count, (ii) observing the disappearance/reduction in occurrences of abnormal cytogenetic markers detected at the time of diagnosis, and/or (iii) observing the disappearance/reduction in occurrences of BCR/ABL mutational copies detected at the time of diagnosis.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the compound of the present disclosure by at least 5%, at least 10%, or at least 30%, up to 50%, up to 60%, or up to 80% of an initial effective amount that is in a range of 0.1-500 mg/kg per body weight of the subject. The increased effective amount may be in a range of 0.105-900 mg/kg, preferably 1-500 mg/kg, more preferably 10-250 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. Alternatively, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for obtaining, characterizing the compounds of formulae (I) and (II), and uses thereof, and are not intended to limit the scope of the claims.

Example 1

Plant Taxonomy

The compound disclosed herein was named as "Tecomaphorbide". Tecomaphorbide was isolated from the leaf methanol extract from the plant *Tecoma stans* (*Stenolobium stans*). *Tecoma* is a species of flowering perennial shrub in the trumpet vine family Bignoniaceae [order (Lamiales), family (Bignoniaceae), tribe (Tecomeae), and genus (*Tecoma*)].

Example 2

Purification of Tecomaphorbide

The fresh leaves of *Tecoma stans* plant was dried at room temperature in a shady place for one month. 5 kg of the air-dried leaves was powdered then soaked in 50 L petroleum ether for 10 days to remove the fatty acids. The remaining plant material was then extracted with ethanol (5×50 L) at room temperature for 10 days. After filtration, the combined ethanol extracts were concentrated under vacuum to yield a crude residue.

The crude residue was partitioned between $CHCl_3$ and $H_2O$ (1:1) solvent system. After $CHCl_3$ and $H_2O$ phase separation, the $CHCl_3$ fraction was collected and dried to form a chloroform crude residue. The chloroform crude residue was partitioned between 10% aqueous methanol and hexane. The polar organic compounds were extracted from water using n-butanol thus forming an aqueous methanol extract.

Example 3

Aqueous-Methanol Extract

The aqueous methanol extract (75 g) was adsorbed on silica gel S (70-230 mesh, Merck) (125 g) and subjected to column chromatography using the same adsorbent (900 g). The column (60×7.0 cm) was packed in benzene and eluted with the same solvent. The polarity of the column was then gradually increased by adding ethyl acetate to the benzene eluent, until pure ethyl acetate was used as the eluent. Fractions collected by this method (141 fractions, 500 mL each) were grouped according to their TLC behaviors into four main groups (TSSMI, TSSMII, TSSMIII, and TSSMIV).

Fraction TSSMI (22.0 g) was adsorbed on 52.0 g silica gel S (70-230 mesh, Merck) and loaded onto a column packed in benzene with the same adsorbent (400 g, 5.0×54 cm). The elution process started with benzene, which was followed by ethyl acetate-benzene gradients, and eventually with pure ethyl acetate as the eluent. The elution process afforded 120 fractions, each of 350 mL. Three compounds were identified from this fraction, including β-sitosterol, benzo[c]oxepin-3[1H]-one, and diisooctyl phthalate.

Fraction TSSMII (16.2 g) was adsorbed on 30.0 g silica gel S (70-230 mesh, Merck) and loaded onto a column packed in benzene with the same adsorbent (350 g, 5.0×44 cm). The elution process started with benzene, which was followed by ethyl acetate-benzene gradients, and eventually with pure ethyl acetate as the eluent. The elution process afforded 100 fractions, each of 350 mL. Two compounds were isolated and identified from this fraction, including oleanolic acid and the compound Tecomaphorbide, which has a chemical structure shown in FIG. 1.

Example 4

Chemical Characterizations of Tecomaphorbide

Tecomaphorbide was obtained as a black solid having M.Wt of 636.74 g/mol. Table 1 summarizes characteristics of chemical identifications via Nuclear Magnetic Resonance (NMR) spectroscopies.

TABLE 1

$^1$H and $^{13}$C NMR spectroscopic data of Tecomaphorbide

| C | $^1$H-NMR (CDCl$_3$) | $^{13}$C-NMR (CDCl$_3$) |
|---|---|---|
| 1 |  | 143.5 |
| 2 |  | 129.6 |
| 2$^1$ | 10.96(1H, s) | 187.6 |
| 3 |  | 137.6 |
| 3$^1$ | 7.88(1H, dd, j = 11.6, 6.2) | 128.6 |
| 3$^{2a}$ | 6.12(1H, dd, J = 1.0. 10.6) | 123.5 |
| 3$^{2b}$ | 6.25(1H, dd, j = 1.0. 16.9) |  |
| 4 |  | 132.1 |
| 5 | 10.14(1H, s) | 101.4 |
| 6 |  | 159.3 |
| 7 |  | 137.8 |
| 7$^1$ | 3.28(3H, s) | 12.1 |
| 8 |  | 146.9 |
| 8$^1$ | 1.64(2H, m) | 18.9 |
| 8$^2$ | 1.04(3H, t, j = 4.0) | 14.1 |
| 9 |  | 151.0 |
| 10 | 9.38(1H, s) | 106.8 |
| 11 |  | 132.7 |
| 12 |  | 132.4 |
| 12$^1$ | 3.56(3H, s) | 12.2 |
| 13 |  | 132.4 |
| 13$^1$ |  | 189.4 |
| 13$^2$ | 6.16(1H, s) | 64.3 |
| 13$^3$ |  | 172.8 |
| 14 |  | 150.7 |
| 15 |  | 104.9 |
| 16 |  | 164.0 |
| 17 | 4.39(1H, m) | 50.1 |
| 17$^{1a}$ | 2.20(1H, m) | 29.6 |
| 17$^{1b}$ | 2.59(1H, m) |  |
| 17$^{2a}$ | 2.22(1H, m) | 21.2 |
| 17$^{2b}$ | 2.46(1H, m) |  |
| 17$^3$ |  | 169.3 |
| 18 | 4.13(1H, d, j = 6.1) | 51.3 |
| 18$^1$ | 1.78(3H, d, j = 7.3) | 23.1 |
| 19 |  | 174.0 |
| 20 | 8.46(1H, s) | 93.4 |
| OCH$_2$ | 3 99(2H, m) | 60.6 |
| CH$_3$ | 1.65(3H, t, j = 7.7)) | 19.4 |
| OCH$_3$ | 3.85(3H, s) | 53.0 |

Example 5

Biological Activities of Tecomaphorbide

The cytotoxicity of Tecomaphorbide was tested against various cultured cell lines. Cells were exposed to various concentrations of Tecomaphorbide (ranging from 0.0 to 4.0 μM) for 12 h. Subsequently, the exposed cells were incubated with MTT reagent for 4 h and the developed color was analyzed spectrophotometrically. IC$_{50}$ was determined from the sigmoidal curve of blotting percentage of cell viability versus the logarithm of concentration in μM using Graphpad Prism 6 program. The determined values summarized in Table 2 are the mean±SD value obtained from three independent trials.

TABLE 2

Cytotoxicity of Tecomaphorbide towards hematological and solid tumor cell lines

| CELL LINE | DISEASE | IC$_{50}$ (μM) |
|---|---|---|
| HL-60 | Human acute promyelocytic leukemia | 0.46 ± 0.11 |
| MOLM-13 | Human acute monocytic leukemia | 0.58 ± 0.17 |
| MV4-11 | Human B myelomonocytic leukemia | 0.62 ± 0.14 |
| Jurkat | Human acute T cell leukemia | 1.21 ± 0.24 |
| K562 | Human chronic myelogenous leukemia | 1.53 ± 0.19 |
| U937 | Human histiocytic lymphoma | 1.38 ± 0.32 |
| MCF-7 | Human breast adenocarcinoma | 2.66 ± 0.48 |
| Caco-2 | Human colorectal adenocarcinoma | 2.83 ± 0.62 |
| PC-3 | Human prostate adenocarcinoma | 1.94 ± 0.35 |

Figure 2:
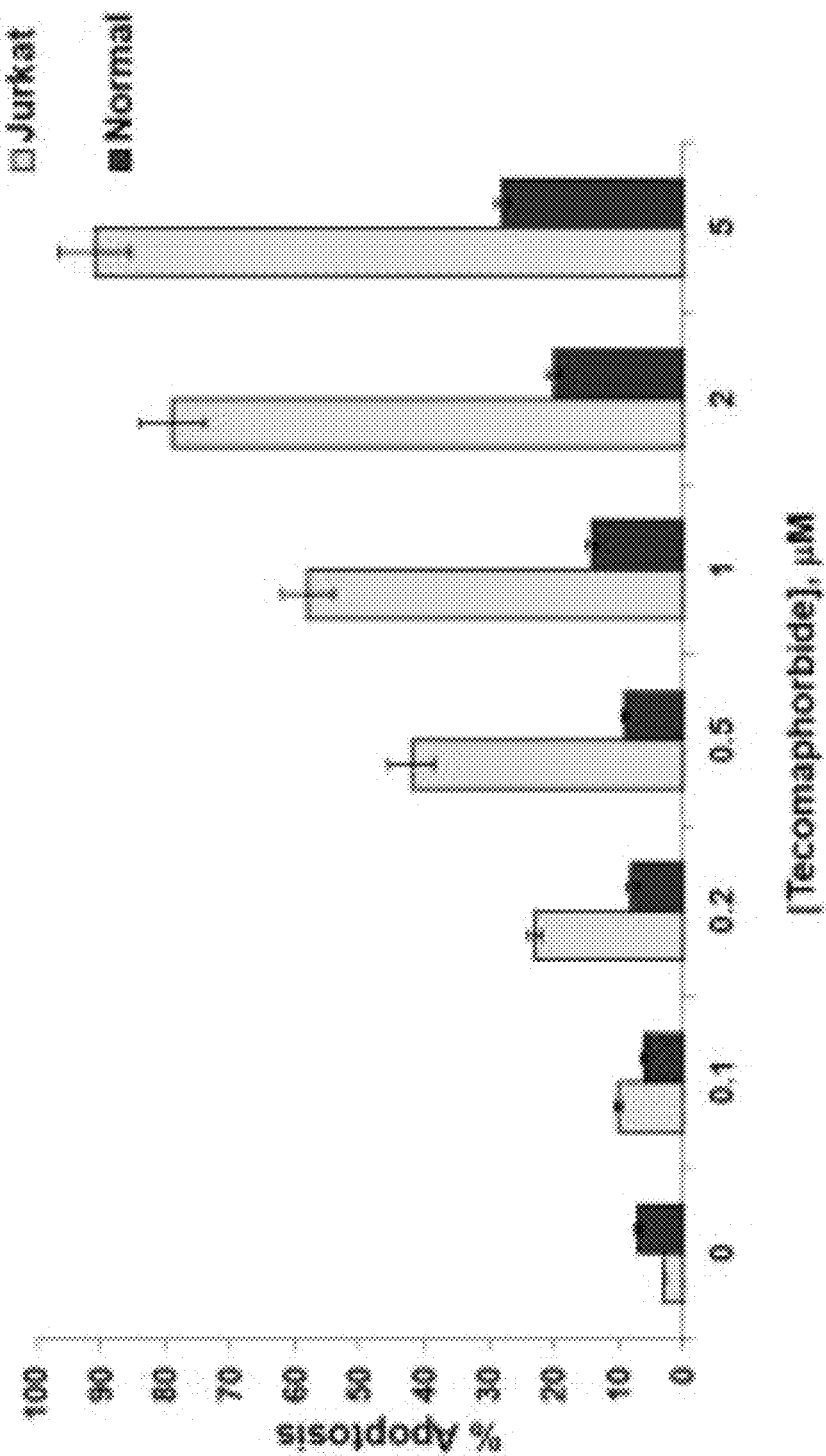
FIG. 2 is a bar graph summarizing the effect of compound Tecomaphorbide on apoptosis in human acute leukemia T-cells (Jurkat cells) and normal primary T-cells.

As shown in FIG. 2, Tecomaphorbide was able to induce apoptosis in T-Cell Acute lymphocytic leukemia cell line (Jurkat) while showed minimal impact on normal primary T-cells. This suggests that the cytotoxicity of the compound targets specifically to cancer cells rather than normal cells.

The invention claimed is:
1. A pharmaceutical composition, comprising:
a compound of formula (I)

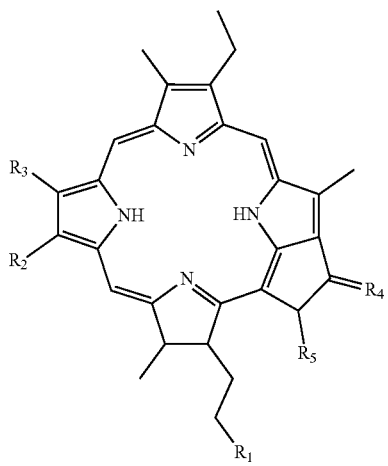

or a salt thereof, a solvate thereof, a tautomer thereof, a stereoisomer thereof, or a mixture thereof; and
an exogenous pharmaceutically acceptable carrier and/or excipient which is not present in *Tacoma stans*, wherein:
$R_1$ and $R_5$ are independently selected from the group consisting of an optionally substituted alkoxycarbonyl, an optionally substituted aryloxycarbonyl, a carboxy, and an optionally substituted carbamyl, with the proviso that $R_1$ is neither —COO(CH$_2$)$_{19}$CH$_3$, nor —COOCH$_2$—CH=C(CH$_3$)—(CH$_2$)$_3$CH(CH$_3$)—(CH$_2$)$_3$CH(CH$_3$)—(CH$_2$)$_3$CH(CH$_3$)$_2$;
$R_2$ is selected from the group consisting of a formyl, a carboxy, an optionally substituted alkoxycarbonyl, an optionally substituted aryloxycarbonyl, an optionally substituted carbamyl, an optionally substituted imine (—CH=NR$_a$), and an optionally substituted hydrazone (—CH=N—NHR$_b$), wherein $R_a$ and $R_b$ are independently selected from the group consisting of a hydrogen, an optionally substituted alkyl, an optionally substituted cycloalkyl, an optionally substituted arylalkyl, and an optionally substituted aryl;
$R_3$ is selected from the group consisting of an ethenyl, a formyl, a carboxy, an optionally substituted alkoxycarbonyl, an optionally substituted aryloxycarbonyl, an optionally substituted carbamyl, and an optionally substituted ethyl (—CR$_c$R$_d$CR$_e$R$_f$R$_g$), wherein $R_c$, $R_d$, $R_e$, $R_f$, and $R_g$ are independently selected from the group consisting of a hydrogen, a halogen, and a hydroxy; and
$R_4$ is =O, =NR$_a$', or =N—NHR$_b$', wherein $R_a$' and $R_b$' are independently selected from the group consisting of a hydrogen, an optionally substituted alkyl, an optionally substituted cycloalkyl, an optionally substituted arylalkyl, and an optionally substituted aryl wherein the composition comprises 0.01-75 wt % of the compound of formula (I) relative to a total weight of the pharmaceutical composition.
2. The pharmaceutical composition of claim 1, wherein $R_1$ is —COOCH$_3$.
3. The pharmaceutical composition of claim 1, wherein $R_2$ is a formyl.

4. The pharmaceutical composition of claim 1, wherein $R_3$ is an ethenyl.
5. The pharmaceutical composition of claim 1, wherein $R_4$ is =O.
6. The pharmaceutical composition of claim 1, wherein $R_5$ is —COOCH$_2$CH$_3$.
7. The pharmaceutical composition of claim 1, wherein the compound of formula (I) is

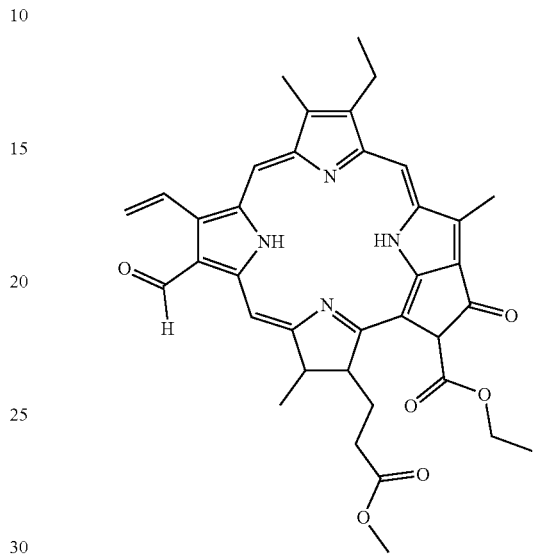

8. The pharmaceutical composition of claim 1, wherein the exogenous pharmaceutically acceptable carrier and/or excipient is at least one selected from the group consisting of an organic solvent, a synthetic polymer, a synthetic fatty ester, and a surfactant.
9. The pharmaceutical composition of claim 1, wherein the exogenous pharmaceutically acceptable carrier and/or excipient is an organic solvent which is at least one selected from the group consisting of acetone, butanone, ethyl acetate, propyl acetate, dimethylformamide, dimethylacetamide, pyrrolidone, N-methyl-2-pyrrolidone, N-(2-hydroxyethyl) pyrrolidone, dimethyl sulfoxide, decylmethyl sulfoxide, tetradecylmethyl sulfoxide, methanol, ethanol, trifluoroethanol, n-propanol, i-propanol, n-butanol, i-butanol, t-butanol, propylene glycol, polyethylene glycol, and poly(tetramethylene ether) glycol.
10. The pharmaceutical composition of claim 1, wherein the exogenous pharmaceutically acceptable carrier and/or excipient is a synthetic polymer selected from the group consisting of a polylactide, a polyglycolide, a polycaprolactone, a polyanhydride, a polyurethane, a polyesteramide, a polyorthoester, a polydioxanone, a polyacetal, a polyketal, a polycarbonate, a polyorthocarbonate, a polyphosphazene, a polyhydroxybutyrate, a polyhydroxyvalerate, a polyalkylene oxalate, a polyalkylene succinate, a poly(malic acid), poly(maleic anhydride), a polyvinyl alcohol, a copolymer thereof, a terpolymer thereof, and combinations thereof.
11. A method of treating a proliferative disorder, the method comprising administering the pharmaceutical composition of claim 1 to a subject in need of therapy; wherein the proliferative disorder is cancer that is selected from the group consisting of leukemia, lymphoma, breast cancer, colon cancer, and prostate cancer.
12. The method of claim 11, wherein the compound of formula (I) is

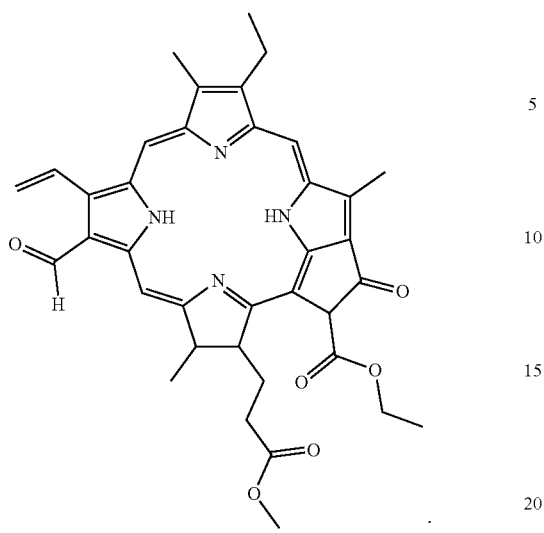
13. The method of claim 11, wherein 0.1-500 mg/kg of the compound of formula (I) is administered per body weight of the subject.
* * * * *